United States Patent
Moon et al.

(10) Patent No.: US 7,816,681 B2
(45) Date of Patent: Oct. 19, 2010

(54) CAPACITIVE GAS SENSOR AND METHOD OF FABRICATING THE SAME

(75) Inventors: Jaehyun Moon, Daejeon (KR); Su Jae Lee, Daejeon (KR); Jin Ah Park, Gyeongsangnam-do (KR); Tae Hyoung Zyung, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 0 days.

(21) Appl. No.: 12/502,824

(22) Filed: Jul. 14, 2009

(65) Prior Publication Data
US 2010/0133528 A1 Jun. 3, 2010

(30) Foreign Application Priority Data
Dec. 3, 2008 (KR) .................. 10-2008-0121625
Mar. 26, 2009 (KR) .................. 10-2009-0025688

(51) Int. Cl.
*H01L 21/28* (2006.01)
*H01L 29/22* (2006.01)

(52) U.S. Cl. ............. 257/43; 257/414; 257/E21.006; 257/E21.158; 257/E29.094; 438/104; 977/921

(58) Field of Classification Search ............ 977/921; 438/104; 257/43, 414, E21.006, E21.158
See application file for complete search history.

(56) References Cited

U.S. PATENT DOCUMENTS

| 4,158,807 A | * | 6/1979 | Senturia | .......... 324/71.1 |
| 4,938,928 A | * | 7/1990 | Koda et al. | .......... 422/98 |
| 7,329,389 B2 | * | 2/2008 | Horovitz et al. | .......... 422/83 |

(Continued)

FOREIGN PATENT DOCUMENTS

KR 10-0325631 2/2002

(Continued)

OTHER PUBLICATIONS

Pike, A et al., "Thermal modelling and characterisation of micropower chemoresistive silicon sensors", Sensors and actuators. B, Chemical, 1997, vol. 45, pp. 19-26.

*Primary Examiner*—Evan Pert
(74) *Attorney, Agent, or Firm*—Rabin & Berdo, P.C.

(57) ABSTRACT

A capacitive gas sensor and a method of fabricating the same are provided. The capacitive gas sensor includes an insulating substrate, a metal electrode and a micro thin-film heater wire integrally formed on the same plane of the insulating substrate, and an oxide detection layer coated on the metal electrode and the micro thin-film heater wire. The fabrication method includes depositing a metal layer on an insulating substrate, etching the metal layer so that a metal electrode and a micro thin-film heater wire form an interdigital transducer on the same plane, and forming a nano crystal complex oxide thin film or a complex oxide nano fiber coating layer on the metal electrode and the micro thin-film heater wire as a detecting layer. The capacitive gas sensor can be easily fabricated and can have excellent characteristics such as high sensitivity, high selectivity, high stability, and low power consumption.

18 Claims, 2 Drawing Sheets

U.S. PATENT DOCUMENTS

| | | |
|---|---|---|
| 7,531,136 B2 * | 5/2009 | Besnard et al. .......... 422/82.02 |
| 2004/0075140 A1 | 4/2004 | Baltes et al. |
| 2008/0128274 A1 | 6/2008 | Raghurama et al. |
| 2009/0148347 A1 * | 6/2009 | Lee et al. ...................... 422/83 |
| 2009/0151429 A1 * | 6/2009 | Jun et al. ................... 73/31.06 |
| 2009/0312954 A1 * | 12/2009 | Utriainen .................... 702/23 |
| 2010/0043881 A1 * | 2/2010 | Ibrahim Alhomoudi et al. ......................... 136/258 |

FOREIGN PATENT DOCUMENTS

| | | |
|---|---|---|
| KR | 2006-0055525 | 5/2006 |
| KR | 2007-0004171 | 1/2007 |
| KR | 10-0812357 | 3/2008 |

* cited by examiner

CAPACITIVE GAS SENSOR AND METHOD OF FABRICATING THE SAME

CROSS-REFERENCE TO RELATED APPLICATION

This application claims priority to and the benefit of Korean Patent Application Nos. 10-2008-0121625, filed Dec. 3, 2008, and 10-2009-0025688 filed Mar. 26, 2009, the disclosure of which is incorporated herein by reference in its entirety.

BACKGROUND

1. Field of the Invention

The present invention relates to a capacitive gas sensor and a method of fabricating the same. More specifically, the present invention relates to a capacitive gas sensor that uses a complex oxide nano structure and simplifies the structure two-dimensionally, and a method of fabricating the same.

2. Discussion of Related Art

A recent increase in concerns about environmental contamination and health remarkably has led to an increase in necessity for detection of harmful gases. Gas sensors originally developed to meet demands for detection of toxic gases and explosive gases are now being developed to meet demands for enhancement of the quality of human life in the fields of health management, environmental monitoring, industrial health and safety, home appliances and home automation, food and agriculture, manufacturing processes, and national defense and terrorism. Therefore, gas sensors may become a means by which a future society free of disasters can be implemented, and more accurate measurement and control of environmentally harmful gases are required.

In order for gas sensors to be practical, high sensitivity, high selectivity, long-term stability, and high response characteristics are required, as are low power consumption and high integration density. In order to satisfy these requirements, gas sensors using various sensor structures and materials and fabrication methods are being developed.

Gas sensors using ceramics are mainly classified into semiconductor gas sensors, solid electrolyte gas sensors, and contact combustion gas sensors, which are distinguished from each other by their types, structures, and materials.

In particular, when oxide semiconductor ceramic such as zinc oxide (ZnO), tin oxide ($SnO_2$), tungsten oxide ($WO_3$), titanium oxide ($TiO_2$), or indium oxide ($In_2O_3$) contacts an environmental gas such as $H_2$, CO, $O_2$, $CO_2$, $NO_x$, a toxic gas, a volatile organic gas, ammonia, an environmental gas, or humidity, electrical resistivity is changed due to adsorption of gases and oxidation/reduction reactions occurring on a surface of the metal oxide. Therefore, studies on resistance type gas sensors using these characteristics are being carried out, and some of the resistance type gas sensors have already been commercialized.

In recent years, many studies on development of gas sensors using physical characteristics of nano structures such as nano thin films, nano particles, nano wires, nano fibers, nano tubes, nano pores, and nano belts different from the characteristics of bulk materials are under way. Small sizes and extremely large surface-to-volume ratios of the nano structures enable manufacture of sensors of rapid reaction time and ultra-high sensitivity. The new materials enable development of gas sensors having excellent characteristics such as quick response speed, high sensitivity, high selectivity, and low power consumption.

However, although a resistance type gas sensor using an oxide semiconductor of a nano structure can achieve very high sensitivity, it does not guarantee high selectivity, long-term stability, or high reproducibility due to instable contact resistance and instability to an external environment.

A conventional oxide semiconductor gas sensor includes a substrate, an oxide sensing material, a metal electrode transducer for detecting an electrical signal of a sensor, and a micro thin-film heater. The micro thin-film heater is located on the top or bottom surface of a thin film and has a structure independent from the metal electrode transducer. This makes the fabrication process of the gas sensor complex.

FIG. 1 is a schematic view of a conventional metal oxide semiconductor gas sensor having a membrane structure. The gas sensor of FIG. 1 is fabricated by the following process. First, after a first insulating layer 105 is formed on a support substrate 106, micro thin-film heater wires 103 are disposed on the first insulating layer 105 and then a second insulating layer 104 is formed on the structure. Then, the support substrate 106 is etched to expose the bottom surface of the first insulating layer 105. Here, the etching of the support substrate 106 is carried out to avoid loss of heat and integrate heat. Electrodes 102 and an oxide layer 101 are deposited on the structure.

It can be understood that, when a gas sensor having a micro heater is to be fabricated, a plurality of lithography processes are necessary to realize the micro heater of the gas sensor. Electrical heating wires located in an insulating layer need to be electrically coupled through additional etching and metal deposition processes in order to apply a voltage therethrough. The etching of a support substrate also requires a very complex process. Although a membrane type micro heater is excellent in collection of heat, a silicon wafer needs to be etched by its general thickness, i.e. 600 microns, making the process complex.

Therefore, development of new sensor materials and sensors compensating for the disadvantages of conventional gas sensors realized by oxide semiconductor materials and having excellent characteristics such as high sensitivity, high selectivity, quick response speed, and long-term stability are urgently required.

Metal oxide semiconductor ceramic, a thin film, and a nano structure such as zinc oxide (ZnO), tin oxide ($SnO_2$), tungsten oxide ($WO_3$), titanium oxide ($TiO_2$), or indium oxide ($In_2O_3$) are known as favorable materials for development of resistance type environmental gas sensors using electrical resistivity characteristics varied by adsorption of gases and oxidation/reduction reactions occurring on a surface of the metal oxide when they are in contact with an environmental gas.

In addition, many studies on ceramic mixtures of an oxide of $BaTiO_3$ and metal oxides such as CaO, MgO, NiO, CuO, $SnO_2$, MgO, $La_2O_3$, $Nd_2O_3$, $Y_2O_3$, $CeO_2$, PbO, $ZrO_2$, $Fe_2O_3$, $Bi_2O_3$, $V_2O_5$, $Nb_2O_5$, and $Al_2O_3$ and ceramic mixtures of different metal oxides such as $WO_3$—(ZnO, CuO, NiO, $SnO_2$, MgO, $Fe_2O_3$), NiO—($V_2O_5$, $SrTiO_3$, ZnO, $In_2O_3$, $BaSnO_3$), ZnO—($SnO_2$, $In_2O_3$), and CoO—$In_2O_3$ are under way. The electrostatic capacity or impedance of such a complex oxide material is changed by adsorption of gases and oxidation/reduction reactions occurring on a surface of a metal oxide since it is in contact with an environmental gas, so that the complex oxide material is a favorable material for development of a capacitive gas sensor.

Such a capacitive gas sensor compensates for the disadvantages of conventional resistance type oxide semiconductor gas sensors and is driven by an AC voltage. The capacitive gas sensor enables low power consumption, high sensitivity, high selectivity, quick gas reaction rate, simplification of its fabrication process due to its simple structure, and miniaturization, and particularly enables long-term stability against an external environment and high integration density. In addition, in the capacitive gas sensor, amplification of electrical capacity can be easily realized by an oscillator circuit and price can be lowered due to a simple signal processing circuit.

Accordingly, the present inventors, while studying a capacitive gas sensor, discovered that the capacitive gas sensor can be easily fabricated due to simplification of its structure when a metal electrode and a micro thin-film heater are integrally formed on the same plane, thereby compensating for the disadvantages of conventional resistance type oxide semiconductor gas sensors.

SUMMARY OF THE INVENTION

The present invention is directed to a capacitive gas sensor that has excellent gas reaction characteristics such as high sensitivity, high selectivity, quick response speed and long-term stability while simplifying a complex process of conventional oxide semiconductor gas sensors.

The present invention is also directed to a method of fabricating a capacitive gas sensor that has excellent gas reaction characteristics such as high sensitivity, high selectivity, quick response speed and long-term stability while simplifying a complex process of conventional oxide semiconductor gas sensors.

One aspect of the present invention provides a capacitive gas sensor, comprising: an insulating substrate; a metal electrode and a micro thin-film heater wire integrally formed on the same plane of the insulating substrate; and an oxide detection layer coated on the metal electrode and the micro thin-film heater wire.

The capacitive gas sensor may further include an electrical signal filtering circuit provided on the same plane of the insulating substrate on which the metal electrode and the micro thin-film heater wire are formed to prevent distortion of an electrical signal due to electrical interference between the metal electrode and the micro thin-film heater wire.

The insulating substrate may be selected from the group consisting of an oxide substrate, a ceramic substrate, and a silicon substrate coated with an insulating layer or a glass substrate.

The metal electrode and the micro thin-film heater wire may form an interdigital transducer having two terminals.

The metal electrode and the micro thin-film heater wire may be made of at least one selected from the group consisting of Pt, Ni, W, Ti, and Cr.

The sensing material may be a nano crystal complex oxide thin film or a complex oxide nano fiber obtained by mixing a p-type oxide semiconductor with an n-type oxide semiconductor.

The n-type oxide semiconductor may be selected from the group consisting of ZnO, $TiO_2$, MgO, $V_2O_5$, $Nb_2O_5$, $Ta_2O_5$, $MnO_3$, $WO_3$, $Al_2O_3$, $Ga_2O_3$, $In_2O_2$, $SnO_2$, and $ABO_3$ perovskite ($BaTiO_3$ or $BaTiO_3$ doped with a metal) and the p-type oxide semiconductor may be selected from the group consisting of NiO, CuO, $Y_2O_3$, $La_2O_3$, $CeO_2$, $Mn_2O_3$, $Co_2O_4$, PdO, $Ag_2O$, $Bi_2O_3$, $Sb_2O_3$, $TeO_2$, and $Fe_2O_3$.

Another aspect of the present invention provides a method of fabricating a capacitive gas sensor, comprising: depositing a metal layer on an insulating substrate; etching the metal layer so that a metal electrode and a micro thin-film heater wire form an interdigital transducer on the same plane; and forming a nano crystal complex oxide thin film or a complex oxide nano fiber coating layer on the metal electrode and the micro thin-film heater wire as a detecting layer.

In etching the metal layer, an electrical signal filtering circuit may be provided on the same plane of the insulating substrate on which the metal electrode and the micro thin-film heater wire are formed to prevent distortion of an electrical signal due to electrical interference between the metal electrode and the micro thin-film heater wire.

The nano crystal complex oxide thin film may be formed by one selected from the group including a sputtering method, a pulse laser deposition method, an e-beam deposition method, a sol-gel method, and a spraying method and may have a thickness of 10 to 1000 nm, and the complex oxide nano fiber coating layer may be formed by electrospinning and the nano fiber may have a diameter of 10 to 100 nm.

BRIEF DESCRIPTION OF THE DRAWINGS

The above and other features and advantages of the present invention will become more apparent to those of ordinary skill in the art by describing in detail exemplary embodiments thereof with reference to the attached drawings in which.

DETAILED DESCRIPTION OF EXEMPLARY EMBODIMENTS

Hereinafter, exemplary embodiments of the present invention will be described in detail with reference to the accompanying drawings.

Figure 1:
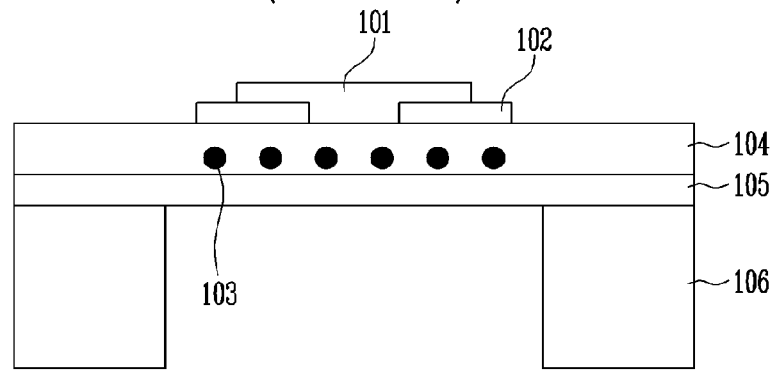
FIG. 1 is a schematic view of a conventional metal oxide semiconductor gas sensor having a membrane structure.
Figure 2:
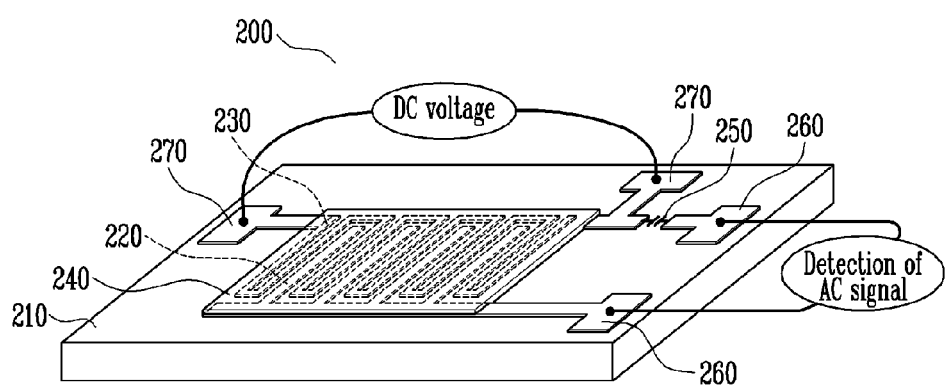
FIG. 2 is a perspective view of a capacitive gas sensor according to an exemplary embodiment of the present invention.
Figure 3:
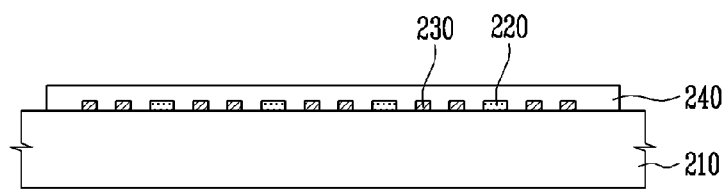
FIG. 3 is a cross-sectional view of the capacitive gas sensor according to an exemplary embodiment of the present invention.

FIG. 2 is a perspective view of a capacitive gas sensor according to an exemplary embodiment of the present invention. FIG. 3 is a cross-sectional view of the capacitive gas sensor according to an exemplary embodiment of the present invention.

Referring to FIGS. 2 and 3, the capacitive gas sensor 200 according to an exemplary embodiment of the present invention includes an insulating substrate 210, a metal electrode 220 and a micro thin-film heater wire 230 integrally formed on the same plane of the insulating substrate 210, and an oxide detection layer 240 coated on the metal electrode 220 and the micro thin-film heater wire 230.

The insulating substrate 210 of the sensor 200 may be made of one selected from the group consisting of an oxide such as $Al_2O_3$, MgO, or $SrTiO_3$, a ceramic material such as $Al_2O_3$ or quartz, silicon ($SiO_2/Si$) coated with an insulating layer, and glass and may have a thickness of 0.1 to 1 mm.

The metal electrode transducer 220 and the micro thin-film heater wire 230 of the gas sensor 200 may be made of at least one selected from the group consisting of Pt, Ni, W, Ti, and Cr and preferably have a thickness of 100 to 500 nm.

The metal electrode transducer 220 and the micro thin-film heater wire 230 of the gas sensor 200 may form an interdigital transducer having two terminals.

The micro thin-film heater wire 230 not only detects an electrical signal of the sensor but also performs the function of a thin-film heater wire.

Electrode pads 270 for applying a DC voltage are provided at opposite ends of the micro thin-film heater wire 230. An electrical signal filtering circuit 250 may be connected to one of the electrode pads 270 of the wire to interrupt the DC voltage and prevent distortion of an electrical sensing signal. Electrode pads 260 for detection of an AC signal, one of which is connected to one end of the electrical signal filtering circuit 250, detect a sensor signal.

The electrical signal filtering circuit 250 for preventing distortion of an electrical signal may employ a DC bias tee and may employ any filtering circuit performing the same function.

The oxide detection layer 240 of the gas sensor 200 may be a nano crystal complex oxide thin film or a complex oxide nano fiber coating layer in which a p-type oxide semiconductor and an n-type oxide semiconductor are mixed.

The nano crystal complex oxide thin film or the complex oxide nano fiber coating layer may be made of an oxide obtained by mixing an n-type oxide semiconductor selected from the group consisting of $ZnO$, $TiO_2$, $MgO$, $V_2O_5$, $Nb_2O_5$, $Ta_2O_5$, $MnO_3$, $WO_3$, $Al_2O_3$, $Ga_2O_3$, $In_2O_2$, $SnO_2$, and $ABO_3$ perovskite ($BaTiO_3$ or $BaTiO_3$ doped with a metal) with a p-type oxide semiconductor selected from the group consisting of $NiO$, $CuO$, $Y_2O_3$, $La_2O_3$, $CeO_2$, $Mn_2O_3$, $Co_2O_4$, $PdO$, $Ag_2O$, $Bi_2O_3$, $Sb_2O_3$, $TeO_2$ and $Fe_2O_3$.

The nano crystal complex oxide thin film may have a thickness of 10 to 1000 nm, and the complex oxide nano fiber may have a diameter of 10 to 100 nm.

Figure 4:
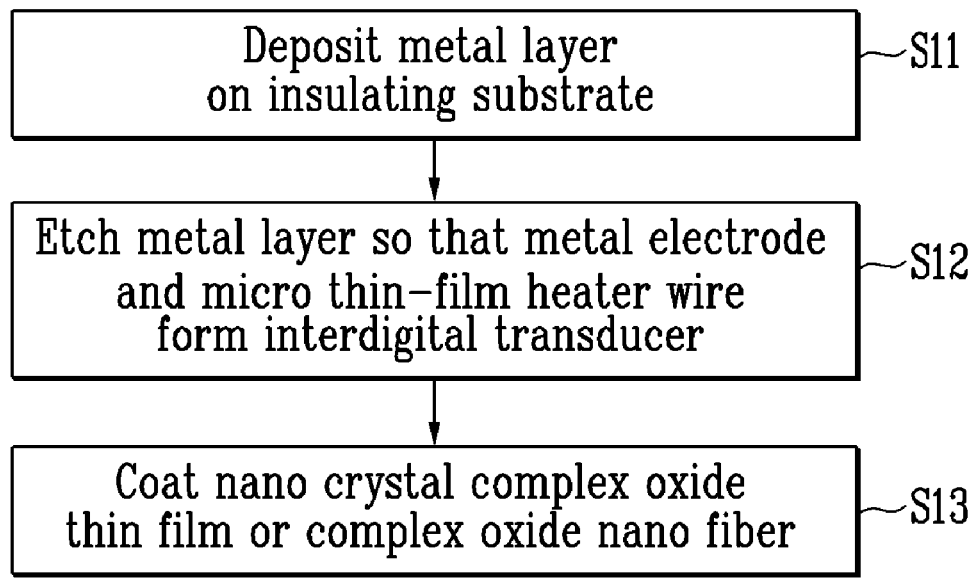
FIG. 4 is a flowchart illustrating a process of fabricating a capacitive gas sensor according to an exemplary embodiment of the present invention.

FIG. 4 is a flowchart illustrating a method of fabricating a capacitive gas sensor according to an exemplary embodiment of the present invention.

Referring to FIG. 4, the method of fabricating a capacitive gas sensor according to an exemplary embodiment of the present invention comprises depositing a metal layer on an insulating substrate (S11), etching the metal layer so that a metal electrode and a micro thin-film heater wire form an interdigital transducer on the same plane (S12), and forming a nano crystal complex oxide thin film or a complex oxide nano fiber coating layer on the metal electrode and the micro thin-film heater wire as a detection layer (S13).

In depositing the metal layer on the insulating substrate (S11), the metal electrode 220 and the micro thin-film heater wire 230 are formed. The metal electrode 220 may be made of at least one selected from the group consisting of Pt, Ni, W, Ti, and Cr and may be deposited by E-beam deposition or sputtering deposition to have a thickness of 100 to 500 nm.

In etching the metal layer (S12), the metal electrode 220 and the micro thin-film heater wire 230 form an interdigital transducer on the same plane. In this case, the etching may be carried out through a general method in the art, and more preferably, through a lift-off process or a wet-etching process.

Meanwhile, electrode pads 270 for applying a DC voltage are formed at opposite ends of the micro thin-film heater wire 230 and an electrical signal filtering circuit 250 is connected to one of the electrode pads 270 to prevent distortion of an electrical sensing signal. The electrical signal filtering circuit 250 may be etched when a metal layer is etched to form the metal electrode 220 and the micro thin-film heater wire 230.

Since the metal electrode and the micro thin-film heater wire or the electrical signal filtering circuit are formed on the same plane, the number of processes is reduced and the processes are simplified.

In forming the nano crystal complex oxide thin film or the complex oxide nano fiber coating layer on the metal electrode and the micro thin-film heater wire as a detection layer (S13), an oxide may be obtained by mixing an n-type oxide semiconductor with a p-type oxide semiconductor. In this case, the n-type semiconductor may be selected from the group consisting of $ZnO$, $TiO_2$, $MgO$, $V_2O_5$, $Nb_2O_5$, $Ta_2O_5$, $MnO_3$, $WO_3$, $Al_2O_3$, $Ga_2O_3$, $In_2O_2$, $SnO_2$, and $ABO_3$ perovskite ($BaTiO_3$ or $BaTiO_3$ doped with a metal) and the p-type oxide semiconductor may be selected from the group consisting of $NiO$, $CuO$, $Y_2O_3$, $La_2O_3$, $CeO_2$, $Mn_2O_3$, $Co_2O_4$, $PdO$, $Ag_2O$, $Bi_2O_3$, $Sb_2O_3$, $TeO_2$, and $Fe_2O_3$.

The nano crystal complex oxide thin film may be deposited using a sputtering method, a pulse laser deposition method, an E-beam deposition method, a sol-gel method, or a spraying method, and may have a thickness of 10 to 1000 nm.

The complex oxide nano fiber coating layer is formed by coating a complex oxide nano fiber using electrospinning, and the nano fiber may have a diameter of 10 to 100 nm.

In a capacitive gas sensor according to the present invention, since a metal electrode and a micro thin-film heater are formed on the same plane, the number of processes is reduced and the processes are simple.

Furthermore, since the capacitive gas sensor according to the present invention uses a nano crystal complex oxide thin film and a complex oxide nano fiber, electrostatic capacities of which are varied by adsorption of gases and oxidation/reduction reactions occurring on a surface of an oxide due to contact with harmful gases, it has excellent characteristics such as high sensitivity, high selectivity, high stability, and low power consumption.

In the drawings and specification, there have been disclosed typical exemplary embodiments of the invention and, although specific terms are employed, they are used in a generic and descriptive sense only and not for purposes of limitation. As for the scope of the invention, it is to be set forth in the following claims. Therefore, it will be understood by those of ordinary skill in the art that various changes in form and details may be made therein without departing from the spirit and scope of the present invention as defined by the following claims.

What is claimed is:

1. A capacitive gas sensor, comprising:
    an insulating substrate;
    a metal electrode and a micro thin-film heater wire integrally formed on the same plane of the insulating substrate; and
    an oxide detection layer coated on the metal electrode and the micro thin-film heater wire.

2. The capacitive gas sensor of claim 1, further comprising an electrical signal filtering circuit provided on the same plane of the insulating substrate on which the metal electrode and the micro thin-film heater wire are formed to prevent distortion of an electrical signal due to electrical interference between the metal electrode and the micro thin-film heater wire.

3. The capacitive gas sensor of claim 1, wherein the insulating substrate is formed of one selected from the group consisting of oxide, ceramic, silicon coated with an insulating layer and glass.

4. The capacitive gas sensor of claim 2, wherein the insulating substrate is formed of one selected from the group consisting of oxide, ceramic, silicon coated with an insulating layer and glass.

5. The capacitive gas sensor of claim 1, wherein the metal electrode and the micro thin-film heater wire form an interdigital transducer having two terminals.

6. The capacitive gas sensor of claim 2, wherein the metal electrode and the micro thin-film heater wire form an interdigital transducer having two terminals.

7. The capacitive gas sensor of claim 1, wherein the metal electrode and the micro thin-film heater wire are made of at least one selected from the group consisting of Pt, Ni, W, Ti, and Cr.

8. The capacitive gas sensor of claim 2, wherein the metal electrode and the micro thin-film heater wire are made of at least one selected from the group consisting of Pt, Ni, W, Ti, and Cr.

9. The capacitive gas sensor of claim 1, wherein the sensing material is a nano crystal complex oxide thin film or a complex oxide nano fiber obtained by mixing a p-type oxide semiconductor with an n-type oxide semiconductor.

10. The capacitive gas sensor of claim 2, wherein the sensing material is a nano crystal complex oxide thin film or a complex oxide nano fiber obtained by mixing a p-type oxide semiconductor with an n-type oxide semiconductor.

11. The capacitive gas sensor of claim 9, wherein the n-type oxide semiconductor is selected from the group consisting of $ZnO$, $TiO_2$, $MgO$, $V_2O_5$, $Nb_2O_5$, $Ta_2O_5$, $MnO_3$, $WO_3$, $Al_2O_3$, $Ga_2O_3$, $In_2O_2$, $SnO_2$, and $ABO_3$ perovskite ($BaTiO_3$ or $BaTiO_3$ doped with a metal) and the p-type oxide semiconductor is selected from the group consisting of $NiO$, $CuO$, $Y_2O_3$, $La_2O_3$, $CeO_2$, $Mn_2O_3$, $Co_2O_4$, $PdO$, $Ag_2O$, $Bi_2O_3$, $Sb_2O_3$, $TeO_2$, and $Fe_2O_3$.

12. The capacitive gas sensor of claim 10, wherein the n-type oxide semiconductor is selected from the group consisting of $ZnO$, $TiO_2$, $MgO$, $V_2O_5$, $Nb_2O_5$, $Ta_2O_5$, $MnO_3$, $WO_3$, $Al_2O_3$, $Ga_2O_3$, $In_2O_2$, $SnO_2$, and $ABO_3$ a perovskite ($BaTiO_3$ or $BaTiO_3$ doped with a metal) and the p-type oxide semiconductor is selected from the group consisting of $NiO$, $CuO$, $Y_2O_3$, $La_2O_3$, $CeO_2$, $Mn_2O_3$, $Co_2O_4$, $PdO$, $Ag_2O$, $Bi_2O_3$, $Sb_2O_3$, $TeO_2$, and $Fe_2O_3$.

13. A method of fabricating a capacitive gas sensor, comprising:
   depositing a metal layer on an insulating substrate;
   etching the metal layer so that a metal electrode and a micro thin-film heater wire form an interdigital transducer on the same plane; and
   forming a nano crystal complex oxide thin film or a complex oxide nano fiber coating layer on the metal electrode and the micro thin-film heater wire as a detecting layer.

14. The method of claim 13, wherein, in etching the metal layer, an electrical signal filtering circuit is provided on the same plane of the insulating substrate on which the metal electrode and the micro thin-film heater wire are formed to prevent distortion of an electrical signal due to electrical interference between the metal electrode and the micro thin-film heater wire.

15. The method of claim 13, wherein the nano crystal complex oxide thin film is formed by one selected from the group including a sputtering method, a pulse laser deposition method, an e-beam deposition method, a sol-gel method and a spraying method, and has a thickness of about 10 to about 1000 nm.

16. The method of claim 14, wherein the nano crystal complex oxide thin film is formed by one selected from the group including a sputtering method, a pulse laser deposition method, an e-beam deposition method, a sol-gel method and a spraying method, and has a thickness of about 10 to about 1000 nm.

17. The method of claim 13, wherein the complex oxide nano fiber coating layer is formed by an electrospinning method and the nano fiber has a diameter of about 10 to about 100 nm.

18. The method of claim 14, wherein the complex oxide nano fiber coating layer is formed by an electrospinning method and the nano fiber has a diameter of about 10 to about 100 nm.

* * * * *